United States Patent [19]
Wallace et al.

[11] Patent Number: 6,066,325
[45] Date of Patent: *May 23, 2000

[54] FRAGMENTED POLYMERIC COMPOSITIONS AND METHODS FOR THEIR USE

[75] Inventors: Donald G. Wallace, Menlo Park; Cary J. Reich, Los Gatos; Narinder S. Shargill, Dublin; Felix Vega; A. Edward Osawa, both of San Francisco, all of Calif.

[73] Assignee: Fusion Medical Technologies, Inc., Mountain View, Calif.

[*] Notice: This patent is subject to a terminal disclaimer.

[21] Appl. No.: 09/032,370

[22] Filed: Feb. 27, 1998

Related U.S. Application Data

[63] Continuation-in-part of application No. 08/903,674, Jul. 31, 1997, and a continuation-in-part of application No. 08/704,852, Aug. 27, 1996, abandoned.
[60] Provisional application No. 60/050,437, Jun. 18, 1997.
[51] Int. Cl.[7] .............................. A61K 9/00; A61F 13/00; A61F 2/00
[52] U.S. Cl. .......................... 424/400; 424/422; 424/423; 424/426; 524/916
[58] Field of Search .................................... 524/916, 400; 424/426, 423, 422

[56] References Cited

U.S. PATENT DOCUMENTS

| | | | |
|---|---|---|---|
| 4,013,078 | 3/1977 | Feild | 128/303 |
| 4,291,013 | 9/1981 | Wahlig et al. | 424/16 |
| 4,347,234 | 8/1982 | Wahlig et al. | 424/15 |

(List continued on next page.)

FOREIGN PATENT DOCUMENTS

| | | | |
|---|---|---|---|
| 376931 | 7/1990 | European Pat. Off. | C08L 89/06 |
| WO 86/00912 | 2/1986 | WIPO | C08B 37/00 |
| WO 92/21354 | 12/1992 | WIPO | A61K 31/725 |
| WO 92/22252 | 12/1992 | WIPO | A61B 17/00 |
| WO 95/15747 | 6/1995 | WIPO | A61K 9/16 |
| WO 96/06883 | 3/1996 | WIPO | C08J 3/28 |
| WO 96/39159 | 12/1996 | WIPO | A61K 38/00 |

OTHER PUBLICATIONS

Boyers et al., "Reduction of postoperative pelvic adhesions in the rabbit with Gore–Tex surgical membrane" *Fert. Ster.* (1988) 49(6):1066–1070.

Heller et al., "Release of Norethindrone from Poly(Ortho Esters)" *Polymer Engineering Sci.* (1981) 21:727–731.

Jeong et al., "Biodegradable block copolymers as injectable drug–delivery systems" *Nature* (1997) 388:860–862.

Langer et al., "Chemical and physical structure of polymers as carriers for controlled release of bioactive agents: A review" *Rev. Marco Chem. Phys.* (1983) C23(1):61–126.

Leong et al., "Polymeric controlled drug delivery" *Adv. Drug Delivery Rev.* (1987) 1:199–233.

Leong et al., "Polyanhydrides for controlled release of bioactive agents" *Biomaterials* (1986) 7:364–371.

Masař et al., "Synthesis of polyurethanes and investigation of their hydrolytic stability" *J. Polymer Sci.* (1979) 66:259–268.

Sidman et al., "Biodegradable, implantable sustained release systems based on glutamic acid copolymers" *J. Membrane Science* (1979) 7:227–291.

*Primary Examiner*—Thurman K. Page
*Assistant Examiner*—Todd D Ware
*Attorney, Agent, or Firm*—Townsend and Townsend and Crew LLP

[57] ABSTRACT

Cross-linked hydrogels comprise a variety of biologic and non-biologic polymers, such as proteins, polysaccharides, and synthetic polymers. Such hydrogels preferably have no free aqueous phase and may be applied to target sites in a patient's body by extruding the hydrogel through an orifice at the target site. Alternatively, the hydrogels may be mechanically disrupted and used in implantable articles, such as breast implants. When used in vivo, the compositions are useful for controlled release drug delivery, for inhibiting post-surgical spinal and other tissue adhesions, for filling tissue divots, tissue tracts, body cavities, surgical defects, and the like.

8 Claims, 5 Drawing Sheets

U.S. PATENT DOCUMENTS

| | | | |
|---|---|---|---|
| 4,749,689 | 6/1988 | Miyata et al. | 514/21 |
| 4,803,075 | 2/1989 | Wallace et al. | 424/423 |
| 4,832,686 | 5/1989 | Anderson | 604/49 |
| 4,925,677 | 5/1990 | Feijen | 424/484 |
| 4,946,870 | 8/1990 | Partain, III et al. | 514/777 |
| 5,007,916 | 4/1991 | Linsky et al. | 606/151 |
| 5,017,229 | 5/1991 | Burns et al. | 106/162 |
| 5,041,292 | 8/1991 | Feijen | 424/484 |
| 5,061,274 | 10/1991 | Kensey | 606/213 |
| 5,061,492 | 10/1991 | Okada et al. | 424/423 |
| 5,080,893 | 1/1992 | Goldberg et al. | 514/0 |
| 5,108,421 | 4/1992 | Fowler | 606/213 |
| 5,126,141 | 6/1992 | Henry | 424/423 |
| 5,129,882 | 7/1992 | Weldon et al. | 604/96 |
| 5,134,229 | 7/1992 | Saferstein et al. | 536/56 |
| 5,135,751 | 8/1992 | Henry et al. | 424/426 |
| 5,140,016 | 8/1992 | Goldberg et al. | 514/57 |
| 5,192,300 | 3/1993 | Fowler | 606/213 |
| 5,196,185 | 3/1993 | Silver et al. | 424/45 |
| 5,204,382 | 4/1993 | Wallace et al. | 523/115 |
| 5,275,616 | 1/1994 | Fowler | 606/213 |
| 5,300,494 | 4/1994 | Brode, II et al. | 514/55 |
| 5,304,377 | 4/1994 | Yamada et al. | 424/426 |
| 5,306,501 | 4/1994 | Viegas et al. | 424/423 |
| 5,330,446 | 7/1994 | Weldon et al. | 604/271 |
| 5,350,573 | 9/1994 | Goldberg et al. | 424/78 |
| 5,352,715 | 10/1994 | Wallace et al. | 523/115 |
| 5,356,614 | 10/1994 | Sharma | 424/45 |
| 5,384,333 | 1/1995 | Davis et al. | 514/772.3 |
| 5,399,361 | 3/1995 | Song et al. | 424/486 |
| 5,418,222 | 5/1995 | Song et al. | 514/21 |
| 5,428,024 | 6/1995 | Chu et al. | 514/21 |
| 5,437,672 | 8/1995 | Allyne | 606/61 |
| 5,447,966 | 9/1995 | Hermes et al. | 523/113 |
| 5,478,352 | 12/1995 | Fowler | 606/213 |
| 5,507,744 | 4/1996 | Tay et al. | 606/50 |
| 5,512,301 | 4/1996 | Song et al. | 424/484 |
| 5,514,379 | 5/1996 | Weissleder et al. | 424/426 |
| 5,516,532 | 5/1996 | Atala et al. | 424/548 |
| 5,531,759 | 7/1996 | Kensey et al. | 606/213 |
| 5,540,715 | 7/1996 | Katsaros et al. | 606/213 |
| 5,648,506 | 7/1997 | Desai et al. | 549/510 |
| 5,672,336 | 9/1997 | Sharma | 424/45 |
| 5,674,275 | 10/1997 | Tang et al. | 607/152 |
| 5,698,213 | 12/1997 | Jamiolkowski et al. | 424/426 |

FRAGMENTED POLYMERIC COMPOSITIONS AND METHODS FOR THEIR USE

The present application is a continuation-in-part of Application Ser. No. 08/903,674, filed on Jul. 31, 1997, which was a continuation-in-part of provisional Application No. 60/050,437, filed on Jun. 18, 1997, and was a continuation-in-part of Application Ser. No. 08/704,852, filed on Aug. 27, 1996, abandoned. The full disclosures of each of these applications are incorporated herein by reference.

BACKGROUND OF THE INVENTION

Field of the Invention

The present invention relates generally to biocompatible cross-linked polymeric compositions and to the use of such compositions for the controlled delivery of aqueous agents to target sites.

It has long been recognized that tablets, capsules, and injections are not the optimum route of drug delivery for all purposes. These conventional routes often require frequent and repeated doses, resulting in a "peak and valley" pattern of therapeutic agent concentration. Since each therapeutic agent has a therapeutic range above which it is toxic and below which it is ineffective, a fluctuating therapeutic agent concentration may cause alternating periods of ineffectiveness and toxicity. For this reason, a variety of "controlled release" drug formulations and devices have been proposed for maintaining the therapeutic agent level within the desired therapeutic range for the duration of treatment. Using a polymeric carrier is one effective means to deliver the therapeutic agent locally and in a controlled fashion. In addition to controlled levels, such systems often require less total drug and minimize systemic side effects.

Polymeric carriers may be biodegradable or non-biodegradable. For a non-biodegradable matrix, the steps leading to release of the therapeutic agent are water diffusion into the matrix, dissolution of the therapeutic agent, and out-diffusion of the therapeutic agent through the channels of the matrix. As a consequence, the mean residence time of the therapeutic agent existing in the soluble state is longer for a non-biodegradable matrix than for a biodegradable matrix where a long passage through the channels is no longer required. Since many pharmaceuticals have short half-lives, there is a significant chance that the therapeutic agent may be decomposed or inactivated inside the non-biodegradable matrix before it can be released. The risk is particularly significant for many biological macromolecules and smaller polypeptides, since these molecules are generally unstable in buffer and have low permeability through polymers. In fact, in a non-biodegradable matrix, many bio-macromolecules will aggregate and precipitate, clogging the channels necessary for diffusion out of the carrier matrix.

These concerns are largely alleviated by using a biodegradable controlled release matrix. Biodegradable polymers release contained drugs as the matrix is consumed or bio-degraded during therapy. The polymer is usually selected to breakdown into subunits which are biocompatible with the surrounding tissue. The persistence of a biodegradable polymer in vivo depends on its molecular weight and degree of cross-linking, the higher the molecular weights and degrees of cross-linking resulting in a longer life. Common biodegradable polymers include polylactic acid (PLA, also referred to as polylactide), polyglycolic acid (PGA), copolymers of PLA and PGA, polyamides, and copolymers of polyamides and polyesters. PLA undergoes hydrolytic de-esterification to lactic acid, a normal product of muscle metabolism. PGA is chemically related to PLA and is commonly used for absorbable surgical sutures, as in the PLA/PGA copolymer. However, the use of PGA in controlled-release implants has been limited due to its low solubility in common solvents and subsequent difficulty in fabrication of devices.

An additional advantage of biodegradable drug delivery carriers is the elimination of the need for surgical removal after it has fulfilled its mission. Additional advantages include: 1) the ability to control release rate through variation of the matrix composition; 2) the ability to implant at sites difficult or impossible for retrieval; 3) an improved ability to deliver unstable therapeutic agents. This last point is of particular importance in light of the advances in molecular biology and genetic engineering which have lead to the commercial availability of many potent biological macromolecules. Such macromolecules usually have short in vivo half-lives and low GI tract absorption which often render them unsuitable for conventional oral or intravenous administration.

Ideally, a biodegradable therapeutic agent delivery system would simply consist of a solution, suspension, or dispersion of the drug in a polymer matrix. The therapeutic agent is released as the polymeric matrix decomposes, or biodegrades into soluble products which are excreted from the body. Unfortunately, the ability to design ideal biodegradable delivery systems is limited by many characteristics of the polymers, including weak mechanical strength, unfavorable degradation characteristics, toxicity, inflexibility, fabrication difficulty, and the like. Although known biodegradable polymers have a broad range of potential utility, there is no one single material available that could satisfy all requirements imposed by different applications. Accordingly, there continues to be need to develop new biodegradable polymers.

U.S. Patent Nos. 5,672,336 and 5,196,185 describe a wound dressing comprising a micro-particulate fibrillar collagen having a particle size of 0.5–2.0 μm. This composition generally comprises an aqueous phase and does not form a hydrogel as described in the present invention. U.S. Pat. No. 5,698,213 describes a cross-linked aliphatic poly-ester hydrogel useful as an absorbable surgical device and drug delivery vehicle. U.S. Pat. No. 5,674,275 describes an acrylate or methacrylate based hydrogel adhesive. U.S. Pat. No. 5,306,501 describes a polyoxyalkylene based thermoreversible hydrogel useful as a drug delivery vehicle.

U.S. Pat. No. 4,925,677 and U.S. Pat. No. 5,041,292 describe a hydrogel comprising a protein component cross-linked with a polysaccharide or mucopolysaccharide and useful as a drug delivery vehicle.

For these reasons, it would be desirable to provide improved compositions, methods, and kits for delivering biological macromolecule and other drugs to target body sites. In particular, it would be desirable to provide compositions which are compatible with a wide variety of drugs either in solution or in suspension, particularly drugs present in an aqueous carrier. Still more preferably, the compositions should be in the form of hydrogels which are biocompatible and which permit substantial control or "programming" of the release characteristics, including release rate, composition persistence, drug carrying capacity, product delivery characteristics (such as injectability), and the like. In addition to drug delivery and release, the products, methods, and kits of the present invention should be adaptable for localizing active agents at a target site, where the active agents can provide biological activity even prior to release from the product matrix. At least some of these objectives will be met by the embodiments of the invention described hereinafter.

Biodegradable injectable drug delivery polymers are described in U.S. Pat. No. 5,384,333 and by Jeong et al. (1997) "Nature," 388:860–862. Biodegradable hydrogels for controlled released drug delivery are described in U.S. Pat. No. 4,925,677. Resorbable collagen-based drug delivery systems are described in U.S. Pat. Nos. 4,347,234 and 4,291,013. Aminopolysaccharide-based biocompatible films for drug delivery are described in U.S. Pat. Nos. 5,300,494 and 4,946,870. Water soluble carriers for the delivery of taxol are described in U.S. Pat. No. 5,648,506.

Polymers have been used as carriers of therapeutic agents to effect a localized and sustained release (Langer, et al., Rev. Macro. Chem. Phys., C23 (1), 61, 1983; Controlled Drug Delivery, Vol. I and II, Bruck, S.D., (ed.), CRC Press, Boca Raton, Fla., 1983; Leong et al., Adv. Drug Delivery Review, 1:199, 1987). These therapeutic agent delivery systems simulate infusion and offer the potential of enhanced therapeutic efficacy and reduced systemic toxicity.

Other classes of synthetic polymers which have been proposed for controlled release drug delivery include polyesters (Pitt, et al., in Controlled Release of Bioactive Materials, R. Baker, Ed., Academic Press, New York, 1980); polyamides (Sidman, et al., Journal of Membrane Science, 7:227, 1979); polyurethanes (Maser, et al., Journal of Polymer Science, Polymer Symposium, 66:259, 1979); polyorthoesters (Heller, et al., Polymer Engineering Scient, 21:727, 1981); and polyanhydrides (Leong, et al., Biomaterials, 7:364, 1986).

Collagen-containing compositions which have been mechanically disrupted to alter their physical properties are described in U.S. Pat. Nos. 5,428,024; 5,352,715; and 5,204,382. These patents generally relate to fibrillar and insoluble collagens. An injectable collagen composition is described in U.S. Pat. No. 4,803,075. An injectable bone/cartilage composition is described in U.S. Pat. No. 5,516,532. A collagen-based delivery matrix comprising dry particles in the size range from 5 $\mu$m to 850 $\mu$m which may be suspended in water and which has a particular surface charge density is described in WO 96/39159. A collagen preparation having a particle size from 1 $\mu$m to 50 $\mu$m useful as an aerosol spray to form a wound dressing is described in U.S. Pat. No. 5,196,185. Other patents describing collagen compositions include U.S. Pat. Nos. 5,672,336 and 5,356,614.

A polymeric, non-erodible hydrogel that may be cross-linked and injected via a syringe is described in WO 96/06883.

The following pending applications, assigned to the assignee of the present application, contain related subject matter: U.S. Ser. No. 08/903,674, filed on Jul. 31, 1997; U.S. Ser. No. 60/050,437, filed on Jun. 18, 1997; U.S. Ser. No. 08/704,852, filed on Aug. 27, 1996; U.S. Ser. No. 08/673,710, filed Jun. 19, 1996; U.S. Ser. No. 60/011,898, filed Feb. 20, 1996; U.S. Ser. No. 60/006,321, filed on Nov. 7, 1996; U.S. Ser. No. 60/006,322, filed on Nov. 7, 1996; U.S. Ser. No. 60/006,324, filed on Nov. 7, 1996; and U.S. Ser. No. 08/481,712, filed on Jun. 7, 1995. The full disclosures of each of these applications is incorporated herein by reference.

SUMMARY OF THE INVENTION

The present invention provides improved biocompatible polymeric compositions and methods for applying such compositions at target sites in a patient's body. The methods and compositions will be particularly useful for delivering drugs and other active agents, such as biological macromolecules, polypeptides, oligopeptides, nucleic acids, small molecule drugs, and the like. The compositions will comprise biocompatible, cross-linked hydrogels, as described in more detail below, and the drug or other biologically active agent will typically be incorporated into the composition as an aqueous solution, suspension, dispersion, or the like. The drugs may be incorporated into the compositions prior to packaging, immediately prior to use, or even as the compositions are being applied to the target site. After introduction to the target site, the drug will usually be released over time as the composition degrades. In some instances, however, the drug or other biological agent may display activity while still incorporated or entrapped within the hydrogel. For example, the compositions and methods may find specific use in stopping or inhibiting bleeding (hemostasis), particularly when combined with a suitable hemostatic agent, such as thrombin, fibrinogen, clotting factors, and the like.

The compositions will have other uses as well, such as tissue supplementation, particularly for filling soft and hard tissue regions, including divots, tracts, body cavities, etc., present in muscle, skin, epithelial tissue, connective or supporting tissue, nerve tissue, ophthalmic and other sense organ tissue, vascular and cardiac tissue, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue. The compositions of the present invention will be still further useful for filling soft implantable devices, such as breast implants, where the material will be protected from cellular or enzyme degradation by a protective barrier or cover. The compositions will additionally be useful in other procedures where it is desirable to fill a confined space with a biocompatible and resorbable polymeric material. Additionally, the compositions may also find use for inhibiting the formation of tissue adhesions, such as spinal tissue adhesions, following surgery and traumatic injury.

The compositions of the present invention comprise a biocompatible, molecular cross-linked hydrogel. Usually the compositions will have substantially no free aqueous phase as defined herein below. The hydrogel is resorbable and fragmented, i.e. comprises small subunits having a size and other physical properties which enhance the flowability of the hydrogel (e.g. the ability to be extruded through a syringe) and the ability of the hydrogel to otherwise be applied onto and conform to sites on or in tissue, including tissue surfaces and defined cavities, e.g. intravertebral spaces, tissue divots, holes, pockets, and the like. In particular, the fragmented subunits are sized to permit them to flow when the compositions are subjected to stresses above a threshold level, for example when extruded through an orifice or cannula, when packed into a delivery site using a spatula, when sprayed onto the delivery site, or the like. The threshold stresses are typically in the range from $3 \times 10^4$ Pa to $5 \times 10^5$ Pa. The compositions, however, will remain generally immobile when subjected to stresses below the threshold level.

By "biocompatible," it is meant that the compositions will be suitable for delivery to and implantation within a human patient. In particular, the compositions will be non-toxic, non-inflammatory (or will display a limited inflammatory effect which is not inconsistent with their implantation), and be free from other adverse biological effects.

By "biodegradable," it is meant that the compositions will degrade and breakdown into smaller molecular subunits that will be resorbed and/or eliminated by the body over time, preferably within the time limits set forth below.

By "substantially free of an aqueous phase" it is meant that the compositions will be fully or partially hydrated, but will not be hydrated above their capacity to absorb water. In particular, a test for determining whether a composition has a free aqueous phase is set forth in Example 8 below. Hydrogels which are substantially free of an aqueous phase should release less than 10% by weight aqueous phase when subjected to a 10 lb. force in the test, preferably releasing less than 5% by weight, and more preferably less than 1% by weight, and more preferably releasing no discernable aqueous phase and displaying no collapse.

The compositions may be dry, partially hydrated or fully hydrated depending on the extent of hydration. The fully hydrated material will hold from about 400% to about 5000% water or aqueous buffer by weight, corresponding to a nominal increase in diameter or width of an individual particle of subunit in the range from approximately 50% to approximately 500%, usually from approximately 50% to approximately 250%. Thus, the size of particles in the dry powder starting material (prior to hydration) will determine the partially or fully hydrated size of the subunit (depending on the factors described below). Exemplary and preferred size ranges for the dry particles and fully hydrated subunits are as follows:

| | Particle/Subunit Size | |
|---|---|---|
| | Exemplary Range | Preferred Range |
| Dry Particle | 0.01 mm–1.5 mm | 0.05 mm–1 mm |
| Fully Hydrated Hydrogel Subunit | 0.02 mm–3 mm | 0.1 mm–1.5 mm |

Compositions of the present invention will usually be in the form of a dry powder, a partially hydrated hydrogel, or a fully hydrated hydrogel. The dry powder (having a moisture content below 20% by weight) will be useful as a starting material for preparation of the hydrogels, as described below. The partially hydrated hydrogels are useful for applications where it is desired that the material further swell upon application to a moist target site, e.g. a tissue divot. The fully hydrated forms will be useful for applications where in situ swelling is not desired, such as in the spinal column and other areas where nerves and other sensitive structures are present.

The dimensions of the subunits may be achieved in a variety of ways. For example, a cross-linked hydrogel having dimensions larger than the target range (as defined below) may be mechanically disrupted at a variety of points during the production process. In particular, the composition may be disrupted (1) before or after cross-linking of a polymer starting material and (2) before or after hydration of the cross-linked or non-cross-linked polymer starting material, e.g. as a fully or partially hydrated material or as a dry particulate powder. The term "dry" will mean that the moisture content is sufficiently low, typically below 20% by weight water, so that the powder will be free-flowing and that the individual particles will not aggregate. The term "hydrated" will mean that the moisture content is sufficiently high, typically above 50% of the equilibrium hydration level, usually in the range from 70% to 95% of the equilibrium hydration level, so that the material will act as a hydrogel.

Mechanical disruption of the polymer material in the dry state is preferred in cases where it is desired to control the particle size and/or particle size distribution. It is easier to control comminution of the dry particles than the hydrated hydrogel materials, and the size of the resulting reduced particles is thus easier to adjust. Conversely, mechanical disruption of the hydrated, cross-linked hydrogels is generally simpler and involves fewer steps than does comminution of a dry polymer starting material. Thus, the disruption of hydrated hydrogels may be preferred when the ultimate hydrogel subunit size and/or size distribution is less critical.

In a first exemplary production process, a dry, non-cross-linked polymer starting material, e.g. dry gelatin powder, is mechanically disrupted by a conventional unit operation, such as homogenization, grinding, coacervation, milling, jet milling, and the like. The powder will be disrupted sufficiently to achieve dry particle sizes which produce hydrogel subunit sizes in the desired ranges when the product is partially or fully hydrated. The relationship between the dry particle size and the fully hydrated subunit size will depend on the swellability of the polymeric material, as defined further below.

Alternatively, a particulate polymeric starting material may be formed by spray drying. Spray drying processes rely on flowing a solution through a small orifice, such as a nozzle, to form droplets which are released into a countercurrent or co-current gas stream, typically a heated gas stream. The gas evaporates solvent from the liquid starting material, which may be a solution, dispersion, or the like. Use of spray drying to form a dry powder starting material is an alternative to mechanical disruption of the starting material. The spray drying operation will usually produce a non-cross-linked dry powder product which is spherical in shape with a generally uniform particle size. The particles may then be cross-linked, as described below.

In many instances, the mechanical disruption operation can be controlled sufficiently to obtain both the particle size and particle size distribution within a desired range. In other cases, however, where more precise particle size distributions are required, the disrupted material can be further treated or selected to provide the desired particle size distribution, e.g. by sieving, aggregation, or the like. The mechanically disrupted polymeric starting material is then cross-linked as described in more detail below, and dried.

The dried material may be the desired final product, where it may be rehydrated and swollen immediately prior to use. Alternatively, the mechanically disrupted, cross-linked material may be rehydrated, and the rehydrated material packaged for storage and subsequent use. Particular methods for packaging and using these materials are described below.

Where the subunit size of the fragmented hydrogel is less important, the dried polymeric starting material may be hydrated, dissolved, or suspended in a suitable buffer and cross-linked prior to mechanical disruption. Mechanical disruption of the pre-formed hydrogel will typically be achieved by passing the hydrogel through an orifice, where the size of the orifice and force of extrusion together determine the particle size and particle size distribution. While this method is often operationally simpler than the mechanical disruption of dry polymeric particles prior to hydration and cross-linking, the ability to control the hydrogel particle size is much less precise.

In a particular aspect of the mechanical disruption of pre-formed hydrogels, the hydrogels may be packed in a syringe or other applicator prior to mechanical disruption. The materials will then be mechanically disrupted as they are applied through the syringe to the tissue target site, as discussed in more detail below. Alternatively, a non-disrupted, cross-linked polymeric material may be stored in a dry form prior to use. The dry material may then be loaded into a syringe or other suitable applicator, hydrated within the applicator, and mechanically disrupted as the material is delivered to the target site, again typically being through an orifice or small tubular lumen.

The polymer will be capable of being cross-linked and of being hydrated to form a hydrogel, as described in more detail below. Exemplary polymers include proteins selected from gelatin, collagen (e.g. soluble collagen), albumin, hemoglobin, fibrinogen, fibrin, fibronectin, elastin, keratin, laminin, casein and derivatives and combinations thereof. Alternatively, the polymer may comprise a polysaccharide, such as a glycosaminoglycan (e.g., hyaluronic acid or chondroitin sulfate), a starch derivative, a cellulose derivative, a hemicellulose derivative, xylan, agarose, alginate, chitosan, and combinations thereof. As a further alternative, the polymer may comprise a non-biologic hydrogel-forming polymer, such as polyacrylates, polymethacrylates, polyacrylamides, polyvinyl polymers, polylactide-glycolides, polycaprolactones, polyoxyethylenes, and derivatives and combinations thereof.

Cross-linking of the polymer may be achieved in any conventional manner. For example, in the case of proteins, cross-linking may be achieved using a suitable cross-linking agent, such as an aldehyde, sodium periodate, epoxy compounds, and the like. Alternatively, cross-linking may be induced by exposure to radiation, such as $\gamma$-radiation or electron beam radiation. Polysaccharides and non-biologic polymers may also be cross-linked using suitable cross-linking agents and radiation. Additionally, non-biologic polymers may be synthesized as cross-linked polymers and copolymers. For example, reactions between mono- and poly-unsaturated monomers can result in synthetic polymers having controlled degrees of cross-linking. Typically, the polymer molecules will each have a molecular weight in the range from 20 kD to 200 kD, and will have at least one link to another polymer molecule in the network, often having from 1 to 5 links, where the actual level of cross-linking is selected in part to provide a desired rate of biodegradability in the ranges set forth below.

The extent of cross-linking of the polymer has an effect on several functional properties of the hydrogel including extrudability, adsorptiveness of surrounding biological fluids, cohesiveness, ability to fill space, swelling ability and ability to adhere to the tissue site. The extent of cross-linking of the polymeric hydrogel composition may be controlled by adjusting the concentration of cross-linking agent, controlling exposure to cross-linking radiation, changing the relative amounts of mono- and poly-unsaturated monomers, varying reaction conditions, and the like. Typically, the degree of cross-linking is controlled by adjusting the concentration of cross-linking agent.

Exposure to radiation, such as $\gamma$-radiation, may also be carried out in order to sterilize the compositions before or after packaging. When the compositions are composed of radiation-sensitive materials, it will be necessary to protect the compositions from the undesirable effects of sterilizing radiation. For example, in some cases, it will be desirable to add a stabilizer, such as ascorbic acid, in order to inhibit degradation and/or further excessive cross-linking of the materials by free radical mechanisms.

The hydrogel compositions of the present invention will typically have a solids content in the range from 1% by weight to 70% by weight. Optionally, the compositions may comprise at least one plasticizer as described in more detail below. Suitable plasticizers include polyethylene glycols, sorbitol, glycerol, and the like.

The equilibrium swell of the cross-linked polymers of the present invention may range from 400% to 5000%, 400% to 3000%, 400% to 2000%, usually ranging from 400% to 1300%, preferably being from 500% to 1100%, depending on its intended use. Such equilibrium swell may be controlled by varying the degree of cross-linking, which in turn is achieved by varying the cross-linking conditions, such as the type of cross-linking method, duration of exposure of a cross-linking agent, concentration of a cross-linking agent, cross-linking temperature, and the like.

Gelatin-containing hydrogels having equilibrium swell values from about 400% to 1300% were prepared and are described in the Experimental section hereinafter. It was found that materials having differing equilibrium swell values perform differently in different applications. For example, the ability to inhibit bleeding in a liver divot model was most readily achieved with cross-linked gelatin materials having a swell in the range from 600% to 950%, often from 700% to 950%. For a femoral artery plug, lower equilibrium swell values in the range from 500% to 600% were more successful. Thus, the ability to control cross-linking and equilibrium swell allows the compositions of the present invention to be optimized for a variety of uses.

In addition to equilibrium swell, it is also important to control the hydration of the material immediately prior to delivery to a target site. Hydration is defined as the percentage of water contained by the hydrogel compared to that contained by the hydrogel when its fully saturated, that is, at its equilibrium swell. A material with 0% hydration will be non-swollen. A material with 100% hydration will be at its equilibrium water content and fully swollen. Hydrations between 0% and 100% will correspond to swelling between the minimum and maximum amounts. As a practical matter, many dry, non-swollen materials according to the present invention will have some residual moisture content, usually below 20% by weight, more usually from 8% to 15% by weight. When the term "dry" is used herein, it will specify materials having a low moisture content, usually below 20%, often below 10%, and frequently below 5% by weight, where the individual particles are free flowing and generally non-swollen.

Hydration can be adjusted very simply by controlling the amount of aqueous buffer added to a dry or partially hydrated cross-linked material prior to use. Usually, at a minimum, it will be desirable to introduce sufficient aqueous buffer to permit extrusion through a syringe or other delivery device. In other cases, however, it may be desirable to utilize a spatula or other applicator for delivering less fluid materials. The intended use will also help determine the desired degree of hydration. In cases where it is desired to fill or seal a moist cavity, it is generally desirable to employ a partially hydrated hydrogel which can swell and fill the cavity by absorbing moisture from the target site. Conversely, fully or substantially fully hydrated hydrogels are preferred for application in the brain, near the spine, and to target sites near nerves and other sensitive body structures which could be damaged by post-placement swelling. It would also be possible to prepare the hydrogel compositions of the present invention with excess buffer, resulting in a two-phase composition having a fully hydrated hydrogel and a free buffer phase.

A preferred hydrogel material according to the present invention is a gelatin which has been cross-linked to achieve from 600% to 950%, usually 700% to 950% swell at equilibrium hydration. The material will be disrupted to have a hydrogel particle size in the range from 0.01 mm to 1.75 mm, preferably 0.05 mm to 1.0 mm, often 0.05 mm to 0.75 mm, and frequently between 0.05 mm and 0.5 mm, and will preferably be hydrated at a level sufficient to achieve 70% to 100% of the equilibrium swell prior to application to the site.

In some cases, the hydrogel compositions of the present invention may contain a combination of two or more different materials, e.g combinations of proteins and polysaccharides and/or non-biologic polymers, as well as combinations of two or more individual materials from each of the polymer types, e.g. two or more proteins, polysaccharides, etc.

The polymeric compositions of the present invention may also comprise combinations of the disrupted, cross-linked polymer hydrogels described above and non-cross-linked polymeric materials. The disrupted, cross-linked polymeric hydrogels consist of a plurality of subunits having a size determined by preparation method. The size is selected to be useful for packing a confined volume, having both the flowability and the rate of biodegradability described in the Experimental section below. The discrete nature of the cross-linked subunits, however, will leave void areas which may be filled by combination with a non-cross-linked polymeric material. The non-cross-linked polymeric or other filler material may comprise any of the polymeric materials listed above, and may optionally but not necessarily be the same polymeric material which has been cross-linked to form the cross-linked mechanically disrupted hydrogel. The relative amounts of cross-linked polymer and non-cross-linked polymer may vary, typically having a weight ratio in the range from 20:1 to 1:1 (cross-linked polymer:non-cross-linked polymer), usually in the range from 10:1 to 2:1, preferably from 5:1 to 2:1.

The hydrogels of the present application may be applied using a syringe, a spatula, a brush, a spray, manually by pressure, or by any other conventional technique. Usually, the hydrogels will be applied using a syringe or similar applicator capable of extruding the hydrogel through an orifice, aperture, needle, tube, or other passage to form a bead, layer, or similar portion of material. Mechanical disruption of the hydrogels can occur as the hydrogel is extruded through an orifice in the syringe or other applicator, typically having a size in the range from 0.01 mm to 5.0 mm, preferably 0.5 mm to 2.5 mm. Preferably, however, the polymeric hydrogel will be initially prepared from a powder having a desired particle size (which upon hydration yields hydrogel subunits of the requisite size) or will be partially or entirely mechanically disrupted to the requisite size prior to a final extrusion or other application step.

The compositions may be applied at varying degrees of hydration, usually but not necessarily being at least partially hydrated. If applied in a non-hydrated form, the compositions will swell to their full equilibrium swell value, i.e. from about 400% to about 5000% as set forth above. When applied at their full hydration, the compositions will display substantially equilibrium hydration and little or no swelling when applied to tissue. Swelling of the non-hydrated and partially hydrated compositions results from absorption of moisture from the tissue and surroundings to which the composition is being applied.

The present invention still further provides kits comprising any of the hydrated or non-hydrated hydrogel materials described above in combination with written instructions for use (IFU) which set forth any of the methods described above for applying the hydrogel onto a target site on tissue. The composition and written instructions will be included together in a conventional container, such as a box, jar, pouch, tray, or the like. The written instructions may be printed on a separate sheet of paper or other material and packaged on or within the container or may be printed on the container itself. Usually, the composition(s) will be provided in a separate sterile bottle, jar, vial, or the like. When the hydrogel material is non-hydrated, the kit may optionally include a separate container with a suitable aqueous buffer for hydration. Other system components such as the applicator, e.g. syringe, may also be provided.

DESCRIPTION OF THE SPECIFIC EMBODIMENTS

Figure 1:
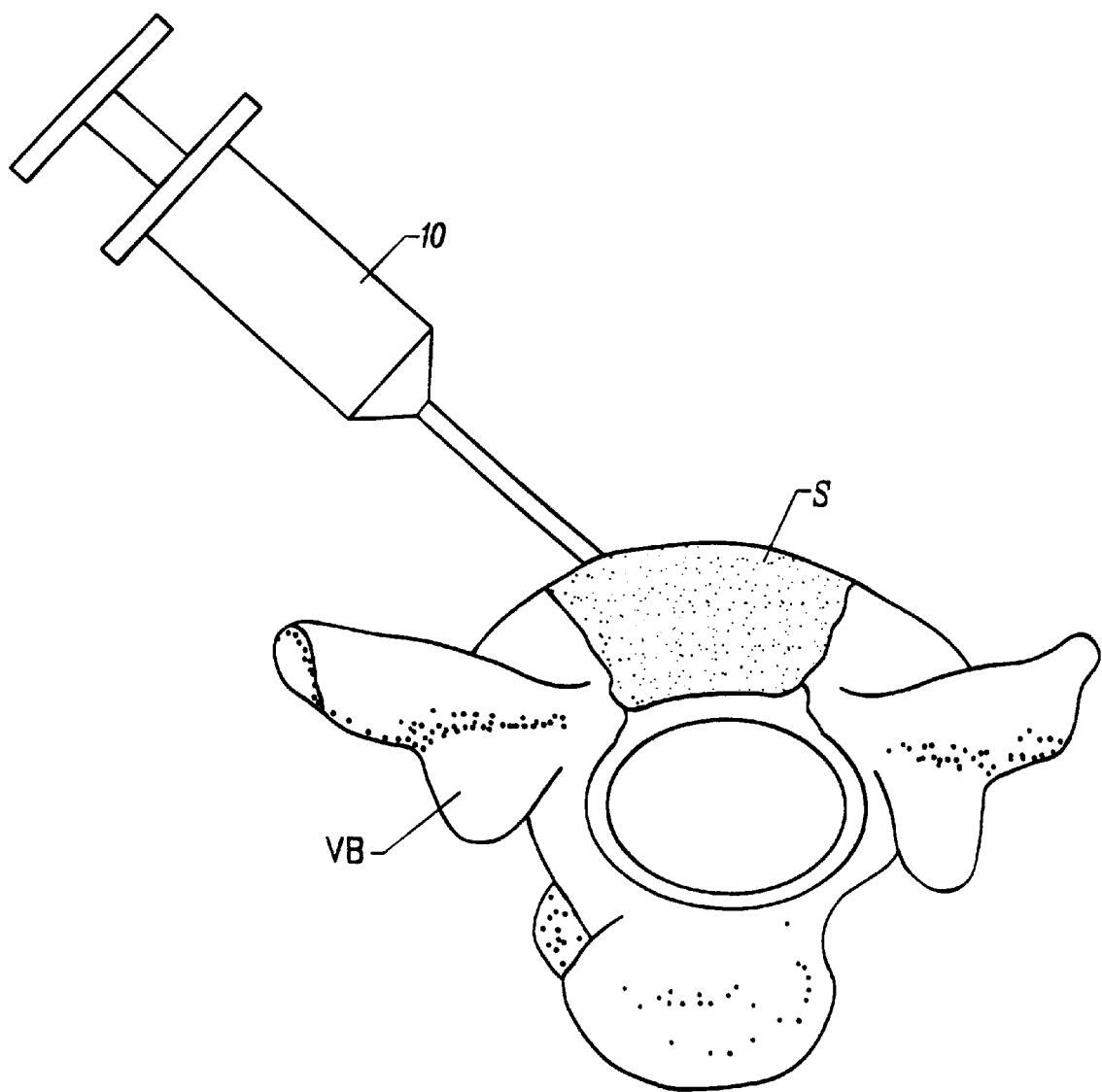
FIG. 1 illustrates the application of the molecular cross-linked polymeric hydrogel of the present invention to a surgically created defect in the vertebral body for preventing post-surgical spinal adhesions.

Compositions according to the present invention comprise resorbable biocompatible molecular cross-linked hydrogels. By "biocompatible" is meant that the materials will meet the criteria in standard # ISO 10993-1 (International Organization for Standardization, Geneva, Switzerland). By "resorbable," it is meant that the compositions will degrade or solubilize, when placed directly into a target site in a patient's body (and not protected within an implant device such as a breast implant), over a time period of less than one year, usually from 1 day to 120 days. A particular protocol for measuring resorption and degradation is set forth in the Experimental section hereinafter. By "molecular cross-linked", it is meant that the materials comprise polymer molecules (i.e. individual chains) which are attached by bridges composed of either an element, a group, or a compound, where the backbone atoms of the polymer molecules are joined by chemical bonds. Cross-linking may be effected in a variety of ways, as will be described in greater detail below.

By "hydrogel," it is meant that the composition comprises a single phase aqueous colloid in which a biologic or non-biologic polymer, as defined in more detail below, absorbs water or an aqueous buffer. The hydrogel comprises multiple sub-networks, where each sub-network is a molecular cross-linked hydrogel having dimensions which depend on the degree of hydration and are within the ranges set forth above. Preferably, the hydrogels will have little or no free water, i.e. water cannot be removed from the hydrogel by simple filtration.

By "percent swell," it is meant that the dry weight is subtracted from the wet weight, divided by the dry weight and multiplied by 100, where wet weight is measured after the wetting agent has been removed as completely as possible from the exterior of the material, e.g. by filtration, and where dry weight is measured after exposure to an elevated temperature for a time sufficient to evaporate the wetting agent, e.g., 2 hours at 120° C.

"Equilibrium swell" is defined as the percent swell at equilibrium after the polymeric material has been immersed in a wetting agent for a time period sufficient for water content to become constant, typically 18 to 24 hours.

"Target site" is the location to which the hydrogel material is to be delivered. Usually, the target site will be the tissue location of interest, but in some cases the hydrogel may be administered or dispensed to a location near the location of interest, e.g. when the material swells in situ to cover the location of interest.

The hydrogels of the present invention may be formed from biologic and non-biologic polymers. Suitable biologic polymers include proteins, such as gelatin, soluble collagen, albumin, hemoglobin, casein, fibrinogen, fibrin, fibronectin, elastin, keratin, laminin, and derivatives and combinations thereof. Particularly preferred is the use of gelatin or soluble non-fibrillar collagen, more preferably gelatin, and exemplary gelatin formulations are set forth below. Other suitable biologic polymers include polysaccharides, such as glycosaminoglycans (e.g. hyaluronic acid and chondroitin sulfate), starch derivatives, xylan, cellulose derivatives, hemicellulose derivatives, agarose, alginate, chitosan, and derivatives and combinations thereof. Suitable non-biologic polymers will be selected to be degradable by either of two mechanisms, i.e. (1) break down of the polymeric backbone or (2) degradation of side chains which result in aqueous solubility. Exemplary nonbiologic hydrogel-forming polymers include synthetics, such as polyacrylates, polymethacrylates, polyacrylamides, polyvinyl resins, polylactide-glycolides, polycaprolactones, polyoxyethylenes, and derivatives and combinations thereof.

The polymer molecules may be cross-linked in any manner suitable to form an aqueous hydrogel according to the present invention. For example, polymeric molecules may be cross-linked using bi- or poly-functional cross-linking agents which covalently attach to two or more polymer molecules chains. Exemplary bifunctional cross-linking agents include aldehydes, epoxies, succinimides, carbodiimides, maleimides, azides, carbonates, isocyanates, divinyl sulfone, alcohols, amines, imidates, anhydrides, halides, silanes, diazoacetate, aziridines, and the like. Alternatively, cross-linking may be achieved by using oxidizers and other agents, such as periodates, which activate side-chains or moieties on the polymer so that they may react with other side-chains or moieties to form the cross-linking bonds. An additional method of cross-linking comprises exposing the polymers to radiation, such as gamma radiation, to activate the side polymer to permit cross-linking reactions. Dehydrothermal cross-linking methods are also suitable. Dehydrothermal cross-linking of gelatin can be achieved by holding it at an elevated temperature, typically 120° C., for a period of at least 8 hours. Increasing the extent of cross-linking, as manifested in a decline in percent swell at equilibrium, can be achieved by elevating the holding temperature, extending the duration of the holding time, or a combination of both. Operating under reduced pressure can accelerate the cross-linking reaction. Preferred methods for cross-linking gelatin molecules are described below.

Optionally, the molecular cross-linked hydrogel may include a plasticizer to increase the malleability, flexibility, and rate of degradation of the hydrogel. The plasticizer may be an alcohol, such as polyethylene glycol, sorbitol, or glycerol, preferably being polyethylene glycol having a molecular weight ranging from about 200 to 1000 D, preferably being about 400 D. The plasticizers will be present in the compositions at from about 0.1% of the solids by weight to about 30% of the solids by weight, preferably from 1% of the solids by weight to 5% of the solids by weight of the composition. The plasticizers are particularly beneficial for use with hydrogels having a high solids content, typically above 10% by weight of the composition (without plasticizer).

Exemplary methods for producing molecular cross-linked gelatins are as follows. Gelatin is obtained and placed in an aqueous buffer to form a non-cross-linked hydrogel, typically having a solids content from 1% to 70% by weight, usually from 3% to 10% by weight. The gelatin is cross-linked, typically by exposure to either glutaraldehyde (e.g. 0.01% to 0.05% w/w, overnight at 0° to 15° C. in aqueous buffer), sodium periodate (e.g. 0.05 M, held at 0° C. to 15° C. for 48 hours) or 1-ethyl-3-(3-dimethylaminopropyl) carbodiimide ("EDC") (e.g., 0.5% to 1.5% w/w, overnight at room temperature), or by exposure to about 0.3 to 3 megarads of gamma or electron beam radiation. Alternatively, gelatin particles can be suspended in an alcohol, preferably methyl alcohol or ethyl alcohol, at a solids content of 1% to 70% by weight, usually 3% to 10% by weight, and cross-linked by exposure to a cross-linking agent, typically glutaraldehyde (e.g., 0.01% to 0.1% w/w, overnight at room temperature). In the case of aldehydes, the pH should be held from about 6 to 11, preferably from 7 to 10. When cross-linking with glutaraldehyde, the cross-links are formed via Schiff bases which may be stabilized by subsequent reduction, e.g. by treatment with sodium borohydride. After cross-linking, the resulting granules may be washed in water and optionally rinsed in an alcohol, dried and resuspended to a desired degree of hydration in an aqueous medium having a desired buffer and pH. The resulting hydrogels may then be loaded into the applicators of the present invention, as described in more detail hereinafter. Alternatively, the hydrogels may be mechanically disrupted prior to or after cross-linking, also as described in more detail hereinafter.

Exemplary methods for producing molecular cross-linked gelatin compositions having equilibrium percent swells in the range from about 400% to about 1300%, preferably 600% to 950%, are as follows. Gelatin is obtained and placed in an aqueous buffer (typically at a pH of 6 to 11, preferably at a pH between 7 and 10) containing a cross-linking agent in solution (typically glutaraldehyde, preferably at a concentration of 0.01% to 0.1% w/w) to form a hydrogel, typically having a solids content from 1% to 70% by weight, usually from 3% to 10% by weight. The hydrogel is well mixed and held overnight at 0°–15° C. as cross-linking takes place. It is then rinsed three times with deionized water, twice with an alcohol (preferably methyl alcohol, ethyl alcohol, or isopropyl alcohol) and allowed to dry at room temperature. Optionally, the hydrogel may be treated with sodium borohydride to further stabilize the cross-linking.

The compositions of the present invention may be further combined with other materials and components, such as bioactive component(s) to be delivered to the patient, viscosity modifiers, such as carbohydrates and alcohols, and other materials intended for other purposes, such as to control the rate of resorption. Exemplary bioactive components include, but are not limited to, proteins, carbohydrates, nucleic acids, and inorganic and organic biologically active molecules such as enzymes, antibiotics, antineoplastic agents, bacteriostatic agents, bacteriocidal agents, antiviral agents, hemostatic agents, local anesthetics, anti-inflammatory agents, hormones, antiangiogenic agents, antibodies, neurotransmitters, psychoactive drugs, drugs affecting reproductive organs and oligonucleotides, such as antisense oligonucleotides. Such bioactive components will typically be present at relatively low concentrations, typically below 10% by weight of the compositions, usually below 5% by weight, and often below 1% by weight. Two or more of such active agents may be combined in a single composition and/or two or more compositions may be used to deliver different active components where said components may interact at the delivery site.

Exemplary hemostatic agents include thrombin, fibrinogen and clotting factors. Hemostatic agents like thrombin may be added in concentrations ranging from 50 to 10,000 Units thrombin per ml hydrogel, preferably from about 100 Units thrombin per ml hydrogel to about 1000 Units thrombin per ml hydrogel.

The molecular cross-linked hydrogels of the present invention can be mechanically disrupted at the time they are delivered to a target site by extrusion through an orifice or other flow restriction, or they can be mechanically disrupted in a batch process prior to delivery to a target site. The primary purpose of this mechanical disruption step is to create multiple subunits of hydrogel having a size which enhances the ability to fill and pack the space to which it is being delivered. Another purpose of the mechanical disruption is to facilitate passage of the hydrogel down small diameter tubes, cannulas, and/or other applicators to the target site. Without mechanical disruption, the molecular cross-linked hydrogels will have difficulty conforming to and filling the irregularly target spaces which are being treated, e.g. intravertebral spaces in the spinal column, tissue divots, percutaneous tissue tracks, and the like. By breaking the hydrogel down to smaller sized sub-units, such spaces can be filled much more efficiently while retaining the mechanical integrity and persistence of the cross-linked hydrogel which are essential for it to act as an anti-adhesive agent, tissue filler, or the like. Surprisingly, it has been found that a single manual extrusion of the composition, typically using a syringe having an orifice in size in the range from 0.01 mm to 5.0 mm, preferably from 0.1 mm to 2.5 mm, provides the proper amount of mechanical disruption to enhance the hydrogel properties as described above.

Alternatively, the hydrogel compositions of the present invention may be mechanically disrupted prior to their final use or delivery. Molecular cross-linking of the polymer chains of the hydrogel can be performed before or after its mechanical disruption. The hydrogels may be mechanically disrupted in batch operations, such as mixing, so long as the hydrogel composition is broken down into sub-units having a size in the 0.01 mm to 5.0 mm range set forth above. When the hydrogel composition is disrupted prior to use, the hydrogel can be applied or administered by techniques other than extrusion e.g. using a spatula, spoon, or the like. Other batch mechanical disruption processes include pumping through a homogenizer or mixer or through a pump which compresses, stretches, or shears the hydrogel to a level which exceeds a fractural yield stress of the hydrogel. In some cases, extrusion of the polymeric composition causes the hydrogel to be converted from a substantially continuous network, i.e. a network which spans the dimensions of the original hydrogel mass, to a collection of sub-networks or sub-units having dimensions in the ranges set forth above. In other cases it may be desirable to partially disrupt the hydrogel compositions prior to packaging in the syringe or other applicator. In such cases, the hydrogel material will achieve the desired sub-unit size prior to final extrusion.

In a presently preferred embodiment, the polymer may be initially prepared (e.g. by spray drying) and/or be mechanically disrupted prior to being cross-linked, often usually prior to hydration to form a hydrogel. The polymer may be provided as a finely divided or powdered dry solid which may be disrupted by further comminution to provide particles having a desired size, usually being narrowly confined within a small range. Further size selection and modification steps, such as sieving, cyclone classification, etc., may also be performed. For the exemplary gelatin materials described hereinafter, the dry particle size is preferably in the range from 0.01 mm to 1.5 mm, more preferably from 0.05 mm to 1.0 mm. An exemplary particle size distribution will be such that greater than 95% by weight of the particles are in the range from 0.05 mm to 0.7 mm. Methods for comminuting the polymeric starting material include homogenization, grinding, coacervation, milling, jet milling, and the like. Powdered polymeric starting materials may also be formed by spray drying. The particle size distribution may be further controlled and refined by conventional techniques such as sieving, aggregation, further grinding, and the like.

The dry powdered solid may then be suspended in an aqueous buffer, as described elsewhere herein, and cross-linked. In other cases, the polymer may be suspended in an aqueous buffer, cross-linked, and then dried. The cross-linked, dried polymer may then be disrupted, and the disrupted material subsequently resuspend in an aqueous buffer. In all the cases, the resulting material comprises a cross-linked hydrogel having discrete sub-networks having the dimensions set forth above.

The compositions of the present invention, after mechanical disruption, will be resorbable, i.e., they will biodegrade in the patient's body, in a period of less than one year, usually from 1 to 120 days, preferably from 1 to 90 days, and more preferably from 2 to 30 days following their initial application. This is particularly true when the materials are used for preventing post-surgical and other adhesions, where a barrier is necessary between the healing tissue surfaces only for so long as the tissue is healing. Techniques for measuring the length of time required for resorption are set forth in Example 11 in the Experimental section below. In other cases, such as when the compositions are contained within an implantable device, such as a breast implant, resorption of the material will be prevented by the membrane or other mechanical barrier surrounding the compositions (unless the integrity of the barrier is broken).

Referring now to FIG. 1, a method for preventing adhesions following a laminectomy procedure will be described. A syringe 10 containing the resorbable molecular cross-linked hydrogel G of the present invention is used to apply the hydrogel in such a manner that all exposed dura in a vertebrae VB is covered. Usually, the hydrogel will be resorbed over a time period in the range from 7 to 60 days.

Figure 2A:
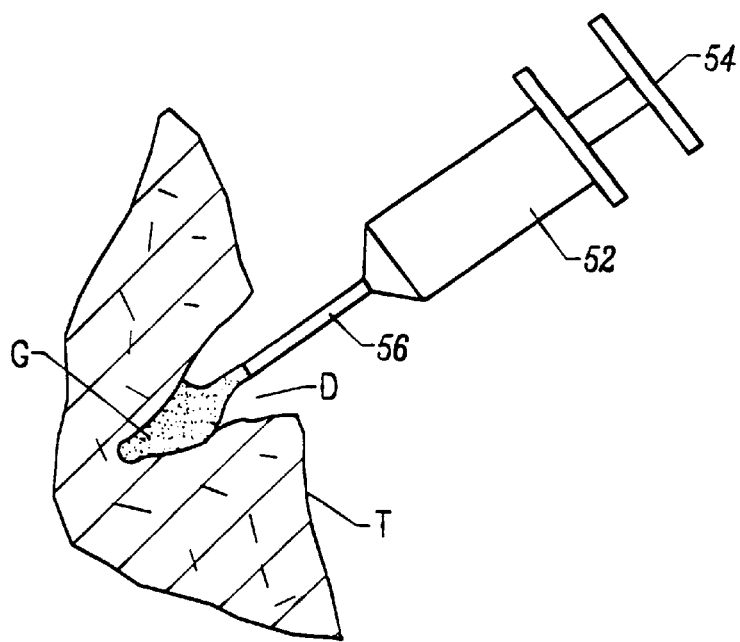
FIGS. 2A and 2B illustrate application of the molecular cross-linked polymeric hydrogel compositions of the present invention to a defect in soft tissue, where the treated region is optionally covered with a protective patch after the defect is filled with the polymeric composition.
Figure 2B:
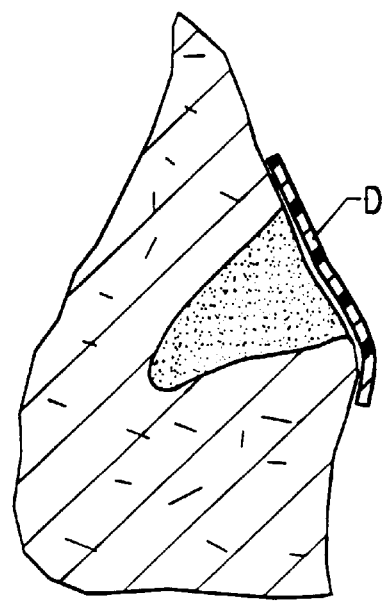

Referring now to FIGS. 2A and 2B, the molecular cross-linked hydrogels of the present invention may also be used to fill divots D in soft tissue T. A syringe 50 comprising a barrel 52, plunger 54 and cannula 56 contains the molecular cross-linked hydrogel in the interior of the barrel 52. The hydrogel G is extruded through the cannula 56 by depressing the plunger 54 in a conventional manner. Sufficient hydrogel is extruded to fill the divot, as shown in FIG. 2B. Preferably, a partially hydrated hydrogel which will swell further upon exposure to the moist tissue environment will be used. It may be desirable to place a patch P over the exposed surface of the hydrogel, as shown in FIG. 2B. The patch may be an adhesive or other conventional self-securing patch. Preferably, however, the patch comprises a collagen, gelatin, or other film that may be immobilized by applying energy e.g. optical or radio frequency energy as described in published PCT applications WO 96/07355 and WO 92/14513.

Figure 3A:
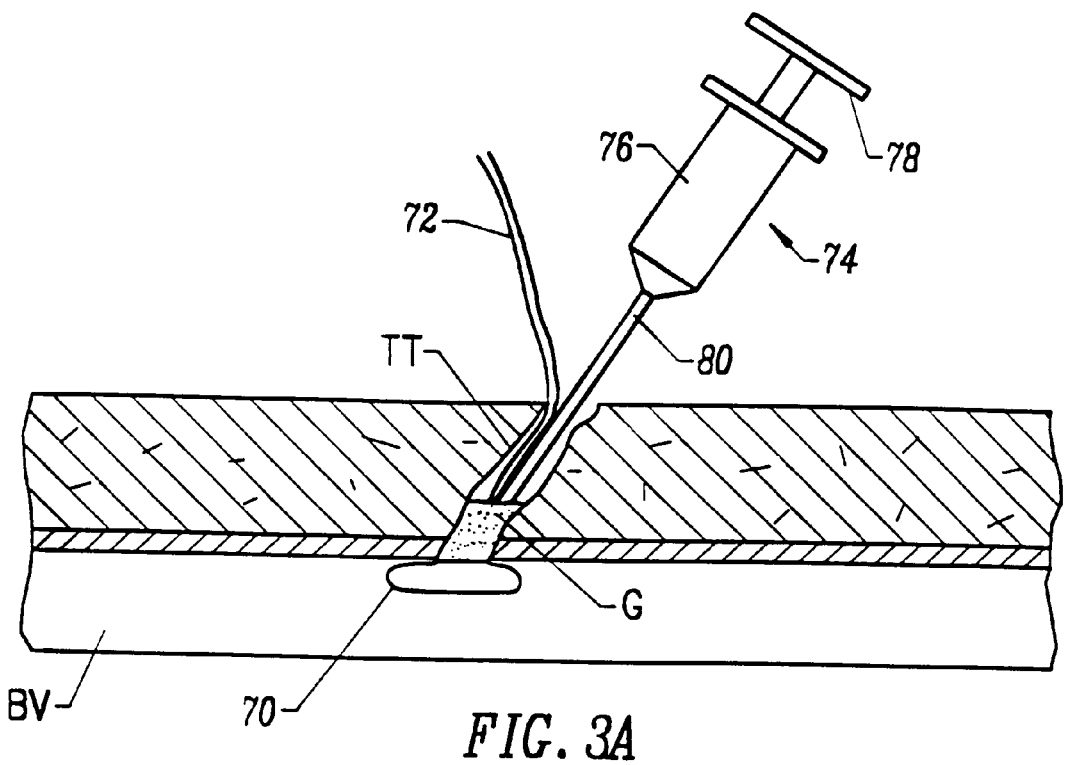
FIGS. 3A and 3B illustrate use of the molecular cross-linked polymeric compositions of the present invention for filling a percutaneous tissue penetration to a blood vessel, such as a tissue tract formed as part of an intravascular catheterization procedure.
Figure 3B:
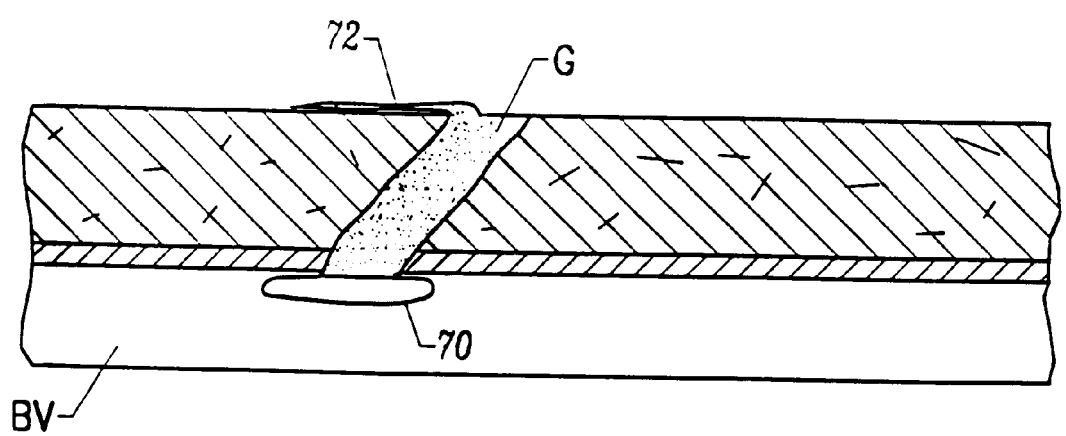

Referring now to FIGS. 3A and 3B, compositions and methods of the present invention may also be used to fill percutaneous tissue tracts TT which were formed through overlying tissue to access blood vessels BV. A barrier element 70 may be placed along the inner wall of the blood vessel at the distal end of the tissue tract TT. Filament 72 may be used to hold the barrier element 70 in place. A syringe 74 comprising a barrel 76, plunger 78, and cannula 80 is then used to extrude the molecular cross-linked hydrogel material of the present invention into the tissue tract over the barrier element 70. The hydrogel G will be used to fill the entire interior volume of the tissue tract TT, as shown in FIG. 3B, and will preferably be partially hydrated to permit post-placement swelling as described above. Optionally, a patch or other cover may be placed over the exposed surface of the tissue tract (not shown). The barrier element 70 may then be removed.

Figure 4:
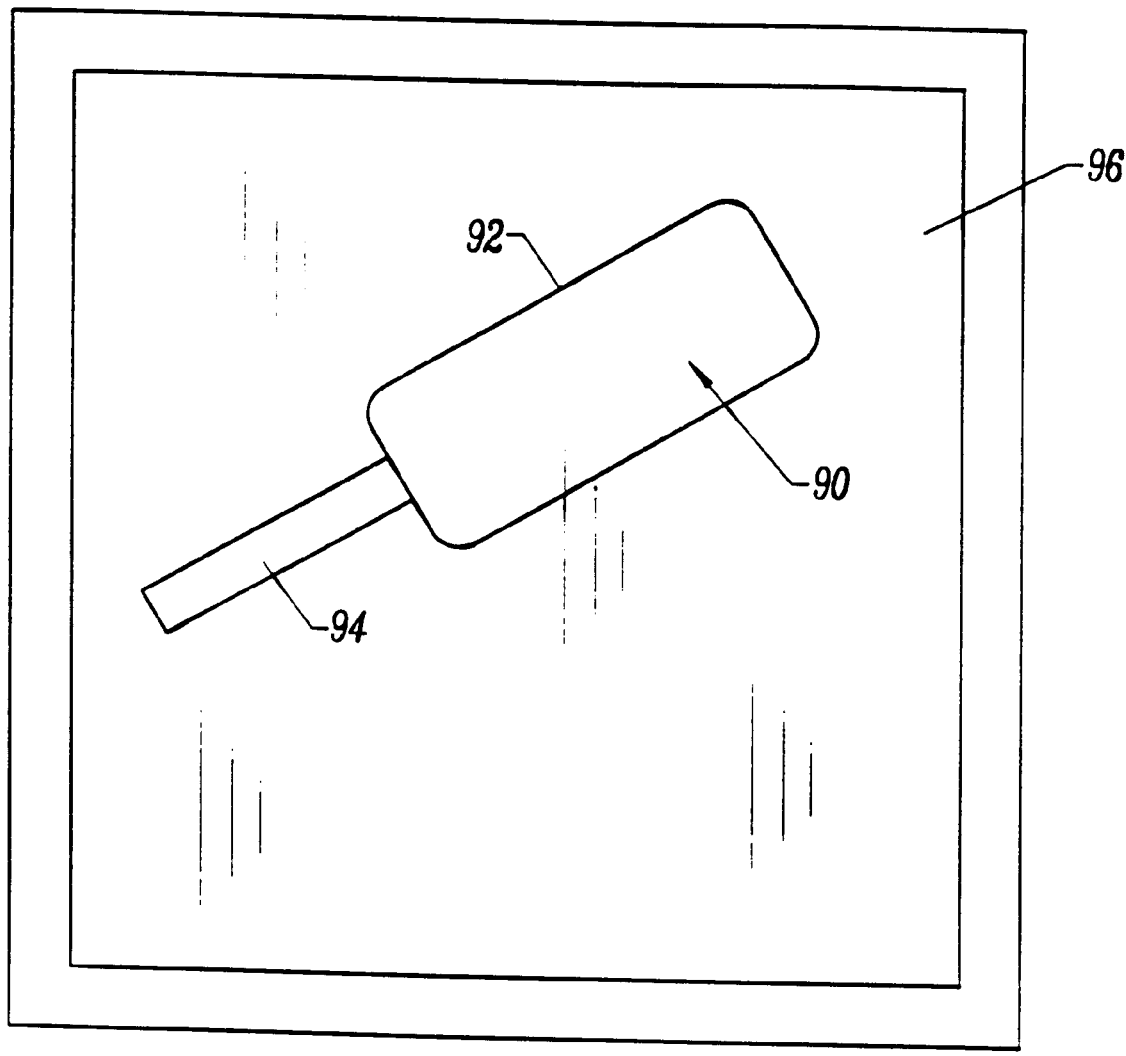
FIG. 4 illustrates a kit comprising a sterile package for an applicator containing the molecular cross-linked polymeric composition of the present invention.
Figure 5:
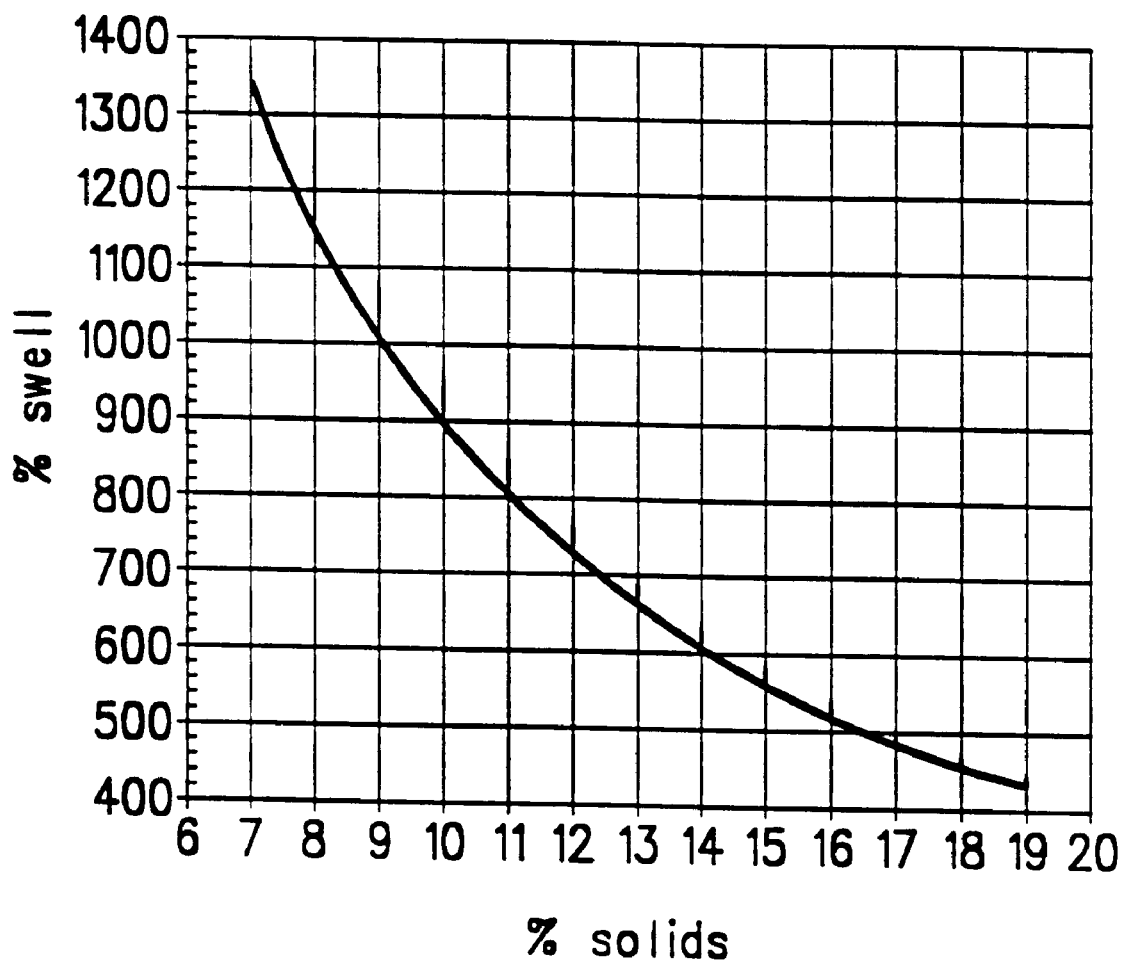
FIG. 5 illustrates the correlation between percent swell and the percent solids of the polymeric hydrogel.

Referring now to FIG. 4, the present invention comprises kits including the hydrated, partially hydrated, and/or non-hydrated polymeric compositions described above packaged in a suitable container, usually with written instructions for use. For example, the composition may be packaged in an applicator 90 which contains the pre-extruded molecular cross-linked hydrogel of the present invention. The applicator may take a wide variety of forms, including syringes as previously described. In FIG. 4, the applicator 90 comprises a tube 92 having a neck 94 which defines an extrusion orifice. The hydrogel is contained within the tube and may be extruded through the neck 94 by squeezing the tube. The applicator 90 is preferably contained in a sterile package 96. The sterile package may take a variety of forms, and is illustrated as an envelope comprising a backing sheet and a clear plastic cover. Such packages may be sterilized in a conventional manner. Optionally, the radiation used to cross-link the hydrogel may also be used to sterilize the entire package. The instructions for use may be printed on the packaging or provided on a separate sheet placed in the package.

The present invention may also be used to inhibit bleeding (cause hemostasis) on an abraded or damaged tissue surface, e.g., any organ surface including the liver, spleen, heart, kidney, intestine, blood vessels, vascular organs, and the like. A syringe containing the resorbable molecular cross-linked hydrogel combined with a hemostasis agent is used to apply the hydrogel to the abraded or damaged tissue site. The hydrogel is applied so that the actively bleeding abraded or damaged area is completely covered with the resorbable molecular cross-linked hydrogel. Suitable hemostatic agents include thrombin, fibrinogen, and other clotting factors, as described for example in U.S. Pat. Nos. 5,411,885; 4,627,879; 4,265,233; 4,298,598; 4,362,567; 4,377,572; and 4,442,655, the disclosures of which are incorporated herein by reference. Conveniently, catalytic components of the hemostasis agent, e.g. thrombin, may be combined in the syringe immediately prior to use so that their combined activities are preserved until applied to the tissue.

When used in regions surrounding nerves and other sensitive body structures, it is preferable to employ fully hydrated hydrogels (i.e. with >95% of hydration at equilibrium swell) in order to avoid damage to the nerves from swelling in an enclosed environment.

The following examples are offered by way of illustration, not by way of limitation.

EXPERIMENTAL

Example 1: Materials and Methods for Production of a Fragmented Polymeric Product Fragmented polymeric compositions are generally prepared as follows:

Using pyrogen-free glassware and distilled water throughout, food grade gelatin (300 Bloom, Atlantic Gelatin, General Foods Corp., Woburn, Mass.) at 10% solids was allowed to swell in 0.1 N aq. sodium hydroxide and 0.05 sodium periodate and held at 0° C. to 8° C. for 2–3 days. The swollen granules were washed in distilled water until the pH reached 8. The neutralized swollen granules were dried in a laminar flow hood and re-suspended in 0.05 M sodium phosphate, 0.15 M sodium chloride, pH 7.2+/−0.2, at 10% solids. The composition was then loaded into 3.0 cc syringes and irradiated at 3.0 megarad with electron beam to sterilize.

Example 2: Materials and Methods for Production of a Fragmented Polymeric Product Gelatin (300 Bloom, Atlantic Gelatin, General Foods Corp., Woburn, Mass.) was allowed to swell in an aqueous buffer (e.g. 0.05 M sodium phosphate, 0.15 M sodium chloride, pH 7.2+/−0.2) at 1–10% solids and was cross-linked by either glutaraldehyde (0.01–0.05%, w/w, overnight, room temperature), by sodium periodate (0.05 M, 0° C. to 8° C., 48 hours) or by 0.3–3.0 megarads of gamma or electron beam irradiation. The hydrogels were then extruded from a syringe using normal manual pressure.

Example 3: Materials and Methods for Production of a Fragmented Polymeric Product Gelatin (300 Bloom, Atlantic Gelatin, General Foods Corp., Woburn, Mass.) was allowed to swell in distilled water at 1–10% solids (w/w) chilled to 5° C. The resultant hydrogel was fragmented by stirring with an impeller driven by a motor. Then, sodium periodate and sodium hydroxide were added and mixed to achieve 0.05 M sodium periodate and 0.10 M sodium hydroxide. The chilled mixture was held at 0° C. to 8° C. for 2–3 days. The cross-linked hydrogel fragments were then washed with 5° C. water to achieve pH 8. Finally the hydrogel fragments were washed with an aqueous buffer (e.g. 0.05 sodium phosphate and 0.15 sodium chloride, pH 7.2+/−0.2) and left at 0° C. to 8° C. to equilibrate with the buffer. Free buffer was decanted from the fragmented hydrogel mass and the hydrogel particles were loaded into syringes and irradiated at 3.0 megarads by electron beam or gamma irradiation to sterilize. Such sterilized fragmented were then extruded directly from the syringe causing further fragmentation.

Example 4: Biocompatibility in Rabbit Model

The test material was prepared by mixing 0.5 mL of sterile saline for injection with 5 mL of the fragmented gelatin composition as follows: The saline solution was injected into the fragmented gelatin composition contained in a 5 cc syringe through a dispersion needle embedded in the fragmented gelatin composition. One mL aliquots of the fragmented gelatin composition were transferred into 1 cc syringe and a 14 gauge needle was attached. The entire assembly was weighed. Following administration of the test article, the syringe and needle assembly were re-weighed to determine the mass of the dosed compound.

A total of 14 rabbits were included in this study. All procedures were performed aseptically. Rabbits were clipped free of fur over the paravertebral muscles. The test material was delivered from a 1 mL syringe with a 14 gauge needle. The needle attached to the syringe containing the test article was inserted into the muscle at a 45° angle. An approximate 0.2 mL portion of the test material was injected into the muscle and needle withdrawn. A total of four test sites were implanted in the right paravertebral muscle of each rabbit. Additionally, a USP negative control strip was implanted as a marker approximately 2–3 mm away from each test site, distal to the vertebral column as compared to the test article. In the opposite (left) muscle, four USP negative control sections were implanted similarly as performed for the markers.

Observations included daily health checks, adverse reactions related to implantation, morbidity and mortality. Body weights were recorded prior to implantation, at monthly intervals, and at termination. At each of the harvest times post-implantation; 2, 4, 6 and 13 weeks, 3 rabbits were euthanized. A gross examination for irritation at each implant site was performed. The paravertebral muscles were dissected free and fixed in 10% neutral buffered formalin. Following appropriate embedding, sectioning and staining, the muscles were evaluated microscopically for evidence of irritation, presence or absence of test article and relative degree of resorption of the implanted test article.

All animals appeared clinically normal throughout the study and gained appropriate weights during the course of the study. At 2 weeks, the inflammatory reaction around the injected test material was localized, with very little extension of this inflammation observed beyond the test material. At four weeks, the inflammatory reaction around the injected test material was localized, with very little extension of this inflammation observed beyond the test material. At four weeks, there was a minimal to mild inflammatory and fibrotic reaction observed at the test sites, which resolved to a minimal reaction at six weeks. By thirteen weeks the inflammatory response was characterized as extremely minimal. The test material was considered to be a non-irritant, compared to the USP negative control material at six and thirteen weeks post implantation.

Example 5: Vessel Plug

This study demonstrated the effectiveness of the fragmented polymeric composition to seal a vessel puncture. The femoral artery of a farm grade Hampshire/Yorkshire cross pig (Pork Power Farms, Turlock, Calif.) was identified and cannulated using a needle (SmartNeedle™, CardioVascular Dynamics, Irvine, Calif.). After the guide wire was placed, a 9 French dilator was used to create a tunnel to the vessel and enlarge the femoral artery opening. The dilator was removed and a 7 French sheath was introduced into the femoral artery. The guide wire was then removed. Positioning was checked by withdrawing blood into the sheath side arm. Pulsatile arterial bleeding was also observed at the point of insertion of sheath at the skin incision. As the sheath was removed, a 18 gauge Teflon catheter tip attached to a hypodermic syringe was used to introduce the fragmented gelatin composition of Example 1 into the tunnel. No bleeding was observed at the point of exit demonstrating the effectiveness of the fragmented gelatin composition in sealing the vessel puncture site and surrounding tissue.

Example 6: Fragmented Polymeric Composition as a Carrier

This study demonstrated the effectiveness of the fragmented polymeric composition of Example 1 as a carrier to fill and seal a tissue divot in the liver. Three wounds (2 tissue divots and 1 tissue puncture) were induced in the liver of a farm grade Hampshire/Yorkshire cross pig (Pork Power Farms, Turlock, Calif.).

Liver tissue divot #1 was actively bleeding following the surgical creation of a tissue divot. A syringe, containing approximately 1 ml of fragmented gelatin composition containing approximately 500 U of thrombin (500 to 1000 units/ml) was extruded from a syringe and applied to completely fill the tissue defect. After 2–3 minutes, a blood clot formed causing immediate cessation of bleeding. When the applied composition was grasped with forceps, it appeared to adhere quite well to the tissue and had good integrity. The sealant was manually challenged and no additional bleeding was observed.

Liver tissue divot #2 was actively bleeding following the surgical creation of a tissue divot. Approximately 1 ml of fragmented gelatin composition containing thrombin (approximately 500 units/ml) was extruded from a syringe and applied to completely fill the tissue defect. A Rapiseal™ patch (Fusion Medical Technologies, Inc., Mountain View, Calif.) was applied over the filled defect using an argon beam coagulator (Valleylab, Boulder, Colo., or Birtcher Medical Systems, Irvine, Calif.,). Immediate cessation of bleeding occurred.

Liver puncture #1, was actively bleeding following the surgical creation of a blunt puncture. Approximately 0.8 ml of fragmented gelatin composition containing thrombin (approximately 500 units/ml) was extruded from a syringe and applied to completely fill the tissue defect. Approximately 2 minutes following the delivery of the fragmented gelatin composition, all bleeding stopped.

Spleen puncture #1 was actively bleeding following the surgical creation of a blunt puncture. Approximately 0.8 ml of fragmented gelatin composition containing thrombin (approximately 500 units/ml) was extruded from a syringe and applied to completely fill the tissue defect. Approximately 2 minutes following the delivery of the fragmented gelatin composition, all bleeding stopped.

In the above four examples, the delivery system used was a 3 cc syringe (Becton Dickinson, Franklin Lakes, N.J.). It contained the fragmented gelatin composition of example 1.

A material according to the present invention for filling tissue divots and other defects could be prepared as follows. A thrombin solution (0.5 ml; 4,000 to 10,000 U/ml) is added to 4.5 ml of flowable hydrogel to produce 5 ml of hydrogel containing 400 to 1000 U/ml thrombin. The hydrogel can be used in any convenient amount, e.g. 0.5 ml to 5 ml.

Example 7: Fragmented Polymeric Composition as a Tissue Filler and Anastomic Sealant This study demonstrated the effectiveness of the fragmented gelatin composition as a wound closure system that fills and seals tissue defects. Four tissue divots were surgically induced, 1 in the lung, 2 in the liver and 1 in the spleen of a farm grade Hampshire/Yorkshire cross pig (Pork Power Farms, Turlock, Calif.).

On the lung, following the surgical creation of the tissue divot, an air leak was observed. Approximately 1 ml of the fragmented gelatin composition of Example 1 was extruded as from a syringe and applied to completely fill the tissue defect. A Rapiseal™ patch (Fusion Medical Technologies, Inc., Mountain View, Calif.) was applied using an argon beam coagulator (Valleylab, Boulder, Colo., or Birtcher Medical Systems, Irvine, Calif.,). Immediate cessation of the air leak occurred. When the applied patch was grasped with forceps, it appeared to adhere quite well to the tissue and had good integrity. The fragmented gelatin composition was challenged by ventilating the lung to a pressure of 28 cm water. No air leak was observed.

On the liver, following the surgical creation of the tissue divot, excessive bleeding was observed. Approximately 1 ml of fragmented gelatin composition was extruded from a syringe and applied to completely fill the tissue defect. The fragmented composition swelled and adequately stopped the bleeding although some seepage bleeding was observed.

On the liver, following the surgical creation of the tissue divot, excessive bleeding was observed. Approximately 1 ml of fragmented gelatin composition was extruded from a syringe and applied to completely fill the tissue defect. A Rapiseal™ patch (Fusion Medical Technologies, Inc., Mountain View, Calif.) was applied using an argon beam coagulator (Valleylab, Boulder, Colo., or Birtcher Medical Systems, Irvine, Calif.,). Immediate cessation of the bleeding occurred. When the applied patch was grasped with forceps, it appeared to adhere quite well to the tissue and had good integrity.

Spleen puncture #1 was actively bleeding following the surgical creation of a blunt puncture. Approximately 0.8 ml of fragmented gelatin composition was extruded from a syringe and applied to completely fill the tissue defect. Approximately 2 minutes following the delivery of the fragmented gelatin composition, all bleeding stopped.

A female juvenile farm grade goat (Clovertop Dairy, Madera, Calif.) was used under appropriate anesthesia. The right cartoid artery was exposed. The vessel was carefully dissected to remove any connective tissue. The vessel was clamped using atraumatic vascular clamps, separated by a distance of approximately 2–3 cm. The vessel was dissected using a standard scalpel blade to expose 2 free vessels ends. An end-to-end anastomosis was created using 6-0 prolene suture in an interrupted fashion. Following completion of the anastomoses, the clamps were released. Bleeding was observed at the anastomotic site. Approximately 2 cc of the fragmented gelatin composition containing thrombin (approximately 500 units/ml) was extruded from a syringe around the anastomoses. Gauze was placed against the composition. Approximately 3 minutes after the application of the fragmented gelatin composition, all bleeding was observed to have ceased. The incision was appropriately closed and the animal was allowed to recover for subsequent follow-up.

Example 8: Materials and Methods for Determining Force Necessary to Release Aqueous Phase Two disks were cut from a filter mesh of sufficient pore size to retain the sample under test. The disks were of approximately the same diameter as the inside of the barrel of a 5 ml syringe (Becton Dickinson, Franklin Lakes, N.J.). The plunger was removed from the 5 ml syringe and the two mesh disks were inserted and pushed into place with the plunger. The plunger was replaced and the syringe placed into an assembly allowing the syringe plunger to be depressed by the force gauge of a Chatillon TCD 200 Test Stand (Chatillon, Greensboro, N.C.). The force required to cause the release of aqueous phase from the test material was then determined.

A 51 $\mu$m stainless steel mesh was used to retain the test materials. The application of 50 lbs. force to 2 ml of the material of Example 4 (above) mixed with reconstituted thrombin (Thrombin-JMI™, GenTrac, Inc., Middelton, Wis.) according to the package insert was insufficient to cause the release of any free liquid, nor any noticeable collapse of the material.

A sterile absorbable gelatin sponge (2.5 ml; Gelfoam®, the UpJohn Co., Kalamazoo, Mich.) was soaked in reconstituted thrombin (Thrombin-JMI™, GenTrac, Inc., Middelton, Wis.) according to the package insert and inserted into the same apparatus as above. The application of less than 1 lb. of pressure caused the release of almost all of the aqueous phase and the collapse of the Gelfoam material to approximately 0.5 mL.

Example 9: Materials and Methods of Ascorbate Addition to Hydrogel Prior to Irradiation Gelatin particles (300 Bloom, Atlantic Gelatin, General Foods Corp., Woburn, Mass.) were suspended at 5%–15% by weight in methyl alcohol (Aldrich, Milwaukee, Wis.) containing 0.01%–0.1% by weight glutaraldehyde (Sigma, St. Louis, Mo.) and stirred overnight at ambient temperature. Alternatively, gelatin particles, obtained from an extract of calf hide (Spears Co., PA) were suspended at 5%–15% by weight in aqueous buffer at pH 9 containing 0.01%–0.1% by weight glutaraldehyde (Sigma) to form a hydrogel that was well-mixed and refrigerated overnight. The cross-linked gelatin fragments were then rinsed three times with alcohol and dried at ambient temperature. Equilibrium swelling for the rinsed, cross-linked gelatin was then measured, and 0.5 g–1.0 g portions of this material were packed into 5 cc syringes. 3.0 ml–4.5 ml of aqueous buffer containing ascorbic acid or a salt of ascorbic acid, e.g. 0.02 M sodium phosphate (J.T. Baker, Phillipsburg, N.J.), 0.15 M sodium chloride (VWR, West Chester, Pa.), 0.005 M sodium ascorbate (Aldrich), pH 7.0, was added to the syringes containing cross-linked gelatin using a second syringe and a three-way stopcock, with care taken not to introduce extraneous air into the syringes, to form a hydrogel within several syringes. Alternatively, an aqueous buffer that did not contain ascorbic acid or a salt of ascorbic acid but was otherwise of similar composition and pH was added to other syringes containing cross-linked gelatin to form a hydrogel within them. The hydrogel-containing syringes were then gamma-irradiated under refrigerated conditions at 3.0±0.3 megarads. Equilibrium swell was measured for the hydrogel contained within the syringes after irradiation. Hydrogels that were formed using buffers that contained ascorbic acid or a salt of ascorbic acid generally maintained values for equilibrium swell upon irradiation within ±20%, and usually ±10%, of the value prior to irradiation, while hydrogels that were formed using buffers not containing ascorbic acid or a salt of ascorbic acid experienced a decrease in equilibrium swell of 25–30% of its value prior to irradiation.

Example 10: Materials and Methods of Cross-Linking and Measuring Percent Swell

Gelatin particles were allowed to swell in an aqueous buffer (e.g., 0.2 M sodium phosphate, pH 9.2) containing a cross-linking agent (e.g., 0.005–0.5% by weight glutaraldehyde). The reaction mixture was held refrigerated overnight and then rinsed three times with deionized water, twice with ethyl alcohol, and allowed to dry at ambient temperature. The dried, cross-linked gelatin was resuspended in an aqueous buffer at a low solids concentration (2–3%) at ambient temperature for a fixed period of time. Buffer was in substantial excess of the concentration needed for equilibrium swelling, and two phases (a hydrogel phase and a buffer) were present. The suspension containing wet hydrogel was then filtered by applying vacuum on a 0.8 μm nominal cut-off filter membrane (Millipore, Bedford, Mass.). After removal of extraneous buffer, the combined weight of the retained wet hydrogel and wet filter membrane was recorded. The hydrogel and membrane were then dried at approximately 120° C. for at least two hours, and the combined weight of the dried hydrogel residue and dried filter membrane was recorded. Several measurements of samples of wet filter membrane without hydrogel residue and dried filter membrane without hydrogel were also performed and were used to deduce the net weight of wet hydrogel and dry hydrogel. "Percent swell" was then calculated as follows:

$$\text{percent swell} = 100 \times \frac{(\text{wet weight of hydrogel} - \text{dry weight of hydrogel})}{\text{dry weight of hydrogel}}$$

Swell measurements were conducted at least in triplicate and averaged for a given sample of gelatin. The value of percent swell for samples resuspended in buffer for 18–24 hr prior to measuring wet weight was defined as "equilibrium swell."

The resulting cross-linked gelatin materials displayed equilibrium swell values in the range from 400% to 1300%. The degree of equilibrium swell depended on the method and extent of cross-linking.

Example 11: Degradation

Thirty rabbits (15 untreated control animals and 15 animals treated with fragmented gelatin composition) underwent surgery to mimic splenic injury and bleeding. A lesion on the spleen was created by making a controlled wound with a 6 mm biopsy punch. In the "Treated" group, the experimentally created injury was immediately treated with the fragmented gelatin composition to cause hemostasis of the wound. "Control" group animals were not treated during the first 7.5 minutes to demonstrate the amount of bleeding resulting from the lesion. At 7.5 minutes from the time the injury was caused, the fragmented gelatin composition was then used to stop bleeding from the lesion to prevent spontaneous exsanguination and death of the animal. All animals were allowed to recover. Ten animals each were euthanized on Days 14 and 28 post-surgery. The final necropsy date for the remaining animals was determined after the Day 28 animals were evaluated. In animals harvested at the Day 28 time point it was difficult to determine via gross examination if the test material was present or not, therefore half of the remaining animals were harvested at Day 42 and the other half at Day 56. At the time of necropsy, the site of the splenic lesion and the peritoneal cavity were evaluated macroscopically. Presence of fragmented gelatin composition in the peritoneal cavity away from the site of placement was noted and evaluated, as well as its presence or absence at the splenic lesion. The presence or absence of postoperative adhesions at the site of the splenic lesion was also evaluated and noted. The spleen was carefully dissected and processed for histological evaluation of biocompatibility and biodegradation.

The application of the fragmented gelatin composition to the surgically created wounds on the spleen resulted in good hemostatic tamponade. Following application of the fragmented gelatin composition at the time of surgery, rabbits were survived for 14, 28, 42, and 56 days postoperatively. One rabbit died of unrelated pneumonia at Day 5 postoperatively and the spleen was not harvested for histopathological examination.

At necropsy, the site of the splenic lesion as well as the peritoneal cavity in general were evaluated grossly. Presence of the fragmented gelatin composition in the peritoneal cavity away from the site of placement was evaluated, as well as the presence or absence of the fragmented gelatin composition at the splenic lesion. The presence or absence of adhesions at the site of the splenic lesion were evaluated and noted. The spleen was carefully dissected and processed for histological evaluation.

Grossly, the site of the splenic lesion was visible in all animals, at all time points. Macroscopically, the fragmented gelatin composition was absent in two of the ten Day 14 animals. At all other time points it was not possible to identify the fragmented gelatin composition macroscopically. The macroscopic absence of the hydrogel material as measured in this rabbit model defines the degradation of the hydrogel as that term is used herein and in the claims.

In three of ten animals sacrificed at 14 days postoperatively, small amounts of the fragmented gelatin composition were found free-floating in the abdominal cavity. This most likely represents the excess material that had migrated from its placement site at the splenic lesion. In no case where this material was found away from the splenic lesion was there any evidence of tissue reaction from the visceral surfaces or the omentum. No material was found away from the site of the splenic lesion in animals that were harvested at any other time point.

No postoperative adhesions associated with the fragmented gelatin composition material were noted at the site of the splenic lesion in any animal. In all animals, as expected, there was omentum attached to the site of the splenic lesion. Other adhesions involving the spleen were rare, and when noted were incidental and usually associated with the incision of the body wall.

The fragmented gelatin composition was absent macroscopically and microscopically in two of the ten animals from the 14 day time point. At 28 days post-implant, the fragmented gelatin composition was not visible on gross observation and microscopically was completely absent in five out of ten rabbits examined and present in minimal amounts in the remaining animals, showing that the fragmented gelatin composition was composition was essentially biodegraded by 28 days. The fragmented gelatin composition was completely absent in all five animals examined at 42 days post-implant and was found in minimal amounts in only one of four rabbits examined at 56 days post-implant. Healing of the splenic wound was proceeding in a normal fashion at Day 42 and more so at Day 56.

Example 12: Fragmented Polymeric Product Composed of Gelatin Cross-Linked Using EDC Gelatin (Atlantic Gelatin, General Foods Corp., Woburn, Mass.) was allowed to dissolve in distilled water at 1–10% solids (w/w) (more preferably at 8%) at 70° C. 1-Ethyl-3-(3dimethylaminopropyl) carbodiimide (EDC) (Sigma, St. Louis, Mo.) at 0.2%–3.5% (more preferably 0.2%–0.3%) was then added. The resultant hydrogel formed on stirring was left at room temperature for one hour. The hydrogel was dried using a Freezone 12 freeze dry system, (Labconco, Mo.) and ground finely using a Waring Blender model No. 31BC91 (VWR, Willard, Ohio). The dried polymeric composition was then loaded into syringes and equilibrated with buffer. The equilibrium swell was determined to be at least 1000% according to the method described in Example 10. The results are shown in Table 1.

TABLE 1

| Gelatin (mg) | EDC | Swell (%) |
|---|---|---|
| 500 (8%) | 13.5 mg (0.25%) | 1080 |
| 500 (8%) | 13.5 mg (0.25%) | 1126 |
| 100 (7.4%) | 0.945 mg (0.35%) | 1620 |
| 100 (7.4%) | 9.45 mg (3.5%) | 1777 |

Example 13: Fragmented Polymeric Product Composed of Gelatin and Poly(L)Glutamic Acid, Cross-Linked Using EDC Gelatin (Atlantic Gelatin, General Foods Corp., Woburn, Mass.) was allowed to dissolve in distilled water at 1–10% solids (w/w) (more preferably at 6–8%) at 70° C. 0–10% (w/w) (more preferably 2–5%) Poly(L)glutamic acid (PLGA) (Sigma, St. Louis, Mo.) and 1-Ethyl-3-(3-dimethylaminopropyl) carbodiimide (EDC) (Sigma) at 0.2–3.5% (preferably 0.2–0.4%) were then added. The resultant hydrogel formed on stirring was left at room temperature for one hour. The hydrogel was allowed to swell in excess saline for a fixed period of time (preferably 20 hr.) The hydrogel was then filtered by applying vacuum on a filter membrane (Millipore, Bedford, Mass.). The equilibrium swell was determined to be at least 1500% according to the method described in Example 10. The results are shown in Table 2.

TABLE 2

| Gelatin (mg) | PLGA (mg) | EDC | Swell (%) |
|---|---|---|---|
| 375 (6%) | 125 (2%) | 13.5 mg (.25%) | 1510 |
| 375 (6%) | 125 (2%) | 13.5 mg (.25%) | 1596 |
| 250 (4%) | 250 (4%) | 13.5 mg (.25%) | 2535 |
| 250 (4%) | 250 (4%) | 13.5 mg (.25%) | 2591 |
| 250 (4%) | 250 (4%) | 13.5 mg (.25%) | 2548 |
| 250 (4%) | 250 (4%) | 13.5 mg (.25%) | 2526 |
| 200 (3.2%) | 300 (4.8%) | 13.5 mg (.25%) | 2747 |
| 200 (3.2%) | 300 (4.8%) | 13.5 mg (.25%) | 2677 |
| 200 (3.2%) | 300 (4.8%) | 13.5 mg (.25%) | 2669 |
| 150 (2.4%) | 350 (5.6%) | 13.5 mg (.25%) | 3258 |
| 150 (2.4%) | 350 (5.6%) | 13.5 mg (.25%) | 3434 |
| 150 (2.4%) | 350 (5.6%) | 13.5 mg (.25%) | 3275 |
| 75 (5.5%) | 25 (1.9%) | 0.945 mg (0.35%) | 2437 |
| 50 (3.7%) | 50 (3.7%) | 0.945 mg (0.35%) | 2616 |
| 25 (1.9%) | 75 (5.5%) | 0.945 mg (0.35%) | 5383 |
| 75 (5.5%) | 25 (1.9%) | 9.45 mg (3.5%) | 1976 |
| 50 (3.7%) | 50 (3.7%) | 9.45 mg (3.5%) | 2925 |
| 25 (1.9%) | 75 (5.5%) | 9.45 mg (3.5%) | 4798 |

Example 14: Production of a Fragmented Polymeric Hydrogel

Bovine Corium (Spears Co. PA) was agitated in an aqueous sodium hydroxide (Spectrum Chemical Co., CA) solution (0.1 M to 1.5 M preferably 0.4 to 1.2M) for a period of one to 18 hours (preferably one to four hours) at a temperature of 2° C. to 30° C. (preferably 22° C. to 30° C.). The corium slurry was then neutralized using an inorganic acid such as hydrochloric acid, phosphoric acid or sulfuric acid (Spectrum Chemical Co., CA.) and the neutralized liquid phase was then separated from the insoluble corium by filtration through a sieve. The corium was then washed with non-pyrogenic water and an alcohol such as isopropyl alcohol (Spectrum Chemical Co., CA.). After three to twelve washes, the corium was suspended in non-pyrogenic water and the corium, water slurry may be then heated to 50° C. to 90° C. preferably 60° C. to 80° C. to thermally gelatinize the corium. During the gelatinization cycle, the pH of the corium, water slurry was adjusted and controlled from pH 3 to pH 11, preferably pH 7 to pH 9. Also, the insoluble corium in the slurry may be disrupted by agitation and/or homogenization. The disruption can occur before or after the thermal gelatinization cycle. Thermal gelatinization was conducted for one to six hours. After gelatinization, the slurry was clarified by filtration. The gelatin slurry was dewatered by drying in air at 15° C. to 40° C., preferably 20° C. to 35° C. The dry gelatin, where dry implies a moisture content less than 20% by weight, was then disrupted by grinding.

Dry gelatin was added to a cold (5° C. to 15° C.) aqueous solution of containing glutaraldehyde (Amresco Inc., OH.) at 0.0025% to 0.075% by weight and at a pH between 7 and 10. The concentration of gelatin in this solution was between 1% and 10% by weight. The glutaraldehyde cross-links the gelatin granules over a period of one to 18 hours after which the gelatin was separated from the aqueous phase by filtration or sedimentation. The gelatin particles were then added to an aqueous solution containing 0.00833% to 0.0667% by weight sodium borohydride (Spectrum Chemical Co., CA.) with the gelatin concentration again being between 1% and 10% by weight and the pH being between 7 and 12, preferably 7 to 9. After one to six hours, the cross-linked gelatin was separated from the aqueous phase by filtration or sedimentation. The gelatin may then be resuspended in non-pyrogenic water with the gelatin concentration being between 1% and 10% by weight to remove residual cross-linking and reducing agents followed by separation from the aqueous phase by filtration or sedimentation. Final collection of the cross-linked gelatin was done on a filter mesh or sieve and the gelatin was given a final rinse with non-pyrogenic water. The wet, cross-linked gelatin was then placed in a drying chamber at 15° C. to 40° C. Dry, cross-linked gelatin (i.e. cross-linked gelatin with a moisture content below 20% by weight) was removed from the drying chamber and then ground using a mechanical, grinding mill to produce a powder with a typical particle size distribution from 0.020 mm to 2.000 mm.

Dry, powdered, cross-linked gelatin was resuspended in a sodium phosphate, sodium chloride and sodium ascorbate buffer at pH 5 to 8 with the gelatin concentration being 10% to 20% by weight. The dry, powdered, cross-linked gelatin may be mixed with the buffer before dispensing the material into the applicator device (i.e. a syringe) or the powdered, cross-linked gelatin may be mixed with the buffer within the applicator device (i.e. a syringe). Additionally, a gas, such as air or nitrogen, may be dispersed with the gelatin and buffer to aid in mixing and dispensing of the material. The gas typically comprised less than 20% by volume of the final mixture.

Powdered, cross-linked gelatin, mixed with buffer and gas within an applicator device was then sealed in the kit to be supplied to the end user. The kits are sterilized by irradiation with gamma-rays or an electron beam.

Although the foregoing invention has been described in some detail by way of illustration and example, for purposes of clarity of understanding, it will be obvious that certain changes and modifications may be practiced within the scope of the appended claims.

What is claimed is:

1. A fragmented biocompatible hydrogel which is at least partially hydrated and is substantially free from an aqueous phase, wherein said hydrogel comprises gelatin and will absorb water when delivered to a moist tissue target site and, wherein the gel has a subunit size in the range from 0.01 mm to 5 mm when fully hydrated and an equilibrium swell from 400% to 5000%, said hydrogel being present in an applicator.

2. The hydrogel of claim 1, having an in vivo degradation time of less than one year.

3. The hydrogel of any of claims 1 and 2, said hydrogel being at least partially hydrated with an aqueous medium comprising an active agent.

4. The hydrogel of claim 3, wherein the active agent is a clotting agent.

5. The hydrogel of claim 4, wherein the clotting agent is thrombin.

6. A method for delivering an active agent to a patient, said method comprising administering to a target site on the patient an amount of the hydrogel of claim 3.

7. A method for delivering a clotting agent to a patient, said method comprising administering from the applicator to a bleeding target site an amount of the hydrogel of claim 4 sufficient to inhibit bleeding.

8. A method for delivering thrombin to a patient, said method comprising administering from the applicator to a bleeding target site an amount of the hydrogel of claim 5 sufficient to inhibit bleeding.

* * * * *